United States Patent [19]

Kelly et al.

[11] Patent Number: 5,593,617
[45] Date of Patent: Jan. 14, 1997

[54] PHOTOCHEMICALLY POLYMERIZABLE LIQUID CRYSTALS

[75] Inventors: Stephen Kelly, Möhlin; Teodor Lukàc, Allschwil, both of Switzerland

[73] Assignee: Hoffmann-LaRoche Inc., Nutley, N.J.

[21] Appl. No.: 517,480

[22] Filed: Aug. 21, 1995

[30] Foreign Application Priority Data

Sep. 12, 1994 [CH] Switzerland ............... 2771/94

[51] Int. Cl.$^6$ .................. C09K 19/20; C09K 19/52; C07C 69/76
[52] U.S. Cl. ................. 252/299.67; 252/299.01; 252/299.61; 252/299.63; 560/61; 560/85
[58] Field of Search .......... 252/299.01, 299.67; 560/61, 85

[56] References Cited

U.S. PATENT DOCUMENTS

| | | | |
|---|---|---|---|
| 4,615,962 | 10/1986 | Garito | 430/28 |
| 5,202,053 | 4/1993 | Shannon | 252/299.01 |
| 5,210,630 | 5/1993 | Heynderickx et al. | 252/299.01 |
| 5,385,690 | 1/1995 | Finkelmann et al. | 252/299.01 |

FOREIGN PATENT DOCUMENTS

| | | |
|---|---|---|
| 331233 | 9/1989 | European Pat. Off. . |
| 611981A1 | 8/1994 | European Pat. Off. . |
| 4233660A1 | 8/1992 | Germany . |
| WO93/22397 | 11/1993 | WIPO . |

OTHER PUBLICATIONS

Sirign, "Plenary Lecture" in Liquid Crystals, vol. 14, No. 1 pp. 15–36, 1993.

Kawakami, et al, Synthesis and Thermal Transition of Side-chain Liquid Crystalline Polyoxetanes Having Laterally Attached Mesogenic Group, Polymer International, vol. 31 pp. 35–40 (1993).

*Primary Examiner*—Shean C. Wu
*Attorney, Agent, or Firm*—George W. Johnston; Patricia S. Rocha-Tramaloni; Raina Semionow

[57] ABSTRACT

The present invention is related to photochemically polymerizable liquid crystals of the general formula

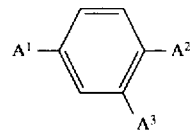

wherein $A^1$, $A^2$ and $A^3$ are, independently, photochemically polymerizable mesogenic residues. The present invention also provides liquid crystalline mixtures which contain these compounds, as well as use of these compounds in the cross-linked state as optical or electronic components.

13 Claims, No Drawings

PHOTOCHEMICALLY POLYMERIZABLE LIQUID CRYSTALS

BACKGROUND OF THE INVENTION

The present invention is related to photochemically polymerizable liquid crystal compounds, liquid crystalline mixtures which contain such compounds, and the use of the liquid crystal compounds in a cross-linked state as optical or electronic components.

Liquid crystals having at least two photochemically polymerizable groups can be orientated on a substrate or in a cell, for example by orientating layers or in a field. These orientated liquid crystals, provided with a suitable mount of a photoinitiator, are polymerized by irradiation with light of a suitable wavelength. The cross-linked structure which is thereby produced remains even at high temperatures. Such layers can be found, for example as, parts of hybrid layers as described in Swiss Patent Applications CH 2016/94 and CH 2017/94. In this manner, optical components such as retarders, wave guides, optical grids and filters, integrated color filters or cells with piezoelectric and with non-linear optical (NLO) properties can be prepared. These types of optical components can be used, for example, in projection systems.

Further, the requirements for properties such as birefringence, refractive index and transparency which must be fulfilled vary depending on the field of application. For example, networks for optical retarders should have a high birefringence in order to keep the layer thickness of the integrated optical component to a minimum.

Polymers which are electrically insulating, but which have a good thermal conductivity, are used in microelectronics to rapidly and efficiently disperse heat which is formed when a high density of components is operated. There is also a need for insulating layers having a low dielectric constant and a high heat resistance. Homogeneously orientated liquid crystalline networks are advantageous for such applications by virtue of their low thermal expansion coefficients, high thermal conductivity and stability.

In addition to the general interest in photochemically polymerizable liquid crystals for optical and electrical components, there is also a need for such compounds in other areas. These liquid crystalline materials are also suitable for cladding glass fibers for optical data transmission. The use of such networks increases the elastic modulus in the longitudinal axis of the fiber, lessens the thermal expansion coefficient and reduces microdistortion losses. This leads to an increased mechanical stability.

Since liquid crystals are usually used as mixtures of several components, it is important that the components have a good miscibility with one another. Conventional photochemically polymerizable liquid crystals usually have a high melting point and clearing point. However, a spontaneous thermal polymerization can occur prematurely in the processing, which is carried out at temperature barely below the clearing point, because at this temperature the viscosity in the liquid crystalline state is at its lowest and is therefore favorable for a good orientatability. This spontaneous polymerisation leads to the formation of domains, whereby the optical and thermal properties in the cross-linked layers produced can be clearly influenced. The melting point can be decreased by producing complicated mixtures with several components, which indeed permits a processing at lower temperatures, but brings with it the danger of a crystallization of conventional polymerizable liquid crystals.

Therefore, it is an object of the present invention to produce photochemically polymerizable compounds having low melting points and clearing points so that they can be processed very readily at temperatures above room temperature in the liquid crystalline state and also in solution. A further object of the present invention is to produce photochemically polymerizable compounds that can be orientated and structured without forming domains. An additional object of the present invention is to produce polymerizable compounds which are thermally stable and have long term stability in the crosslinked state.

SUMMARY OF THE INVENTION

The present invention provides compounds which are suitable as components of liquid crystal mixtures. These compounds have the general formula

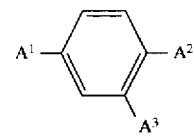

I wherein $A^1$, $A^2$ and $A^3$ are, independently, photochemically polymerizable mesogenic residues.

The mesogenic photochemically polymerizable residues $A^1$, $A^2$ and $A^3$ can be different or the same. These mesogenic residues are provided terminally with a polymerizable residue that makes them suitable for the above-stated objectives.

DETAILED DESCRIPTION

The present invention provides compounds which are outstandingly suitable as components of liquid crystal mixtures. These compounds have the general formula

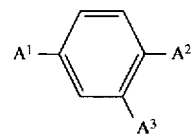

I wherein $A^1$, $A^2$ and $A^3$ are, independently, photochemically polymerizable mesogenic residues.

The mesogenic photochemically oligomerizable or polymerizable residues $A^1$, $A^2$ and $A^3$ can be different or the same. Mesogenic residues are known to persons skilled in the art and are described, for example, in "Flüssigkristalle in Tabellen" Vol. II, Deutscher Verlag für Grundstoffindustrie, Leipzig, 1984. These mesogenic residues of the present invention are provided terminally with a polymerizable residue.

The compounds of general formula I have a good solubility in usual solvents, for example, in anisole, N,N'-dimethylacetamide or N-methylpyrrolidone and are distinguished by a relatively low viscosity. They can therefore be applied to a suitable surface without difficulty, usually by spin-coating. Moreover, since the compounds of the present invention have a liquid crystalline phase, they can be directed, prior to the cross-linking, on an orientating layer or by applying an electric or magnetic field.

Preferred compounds of formula I are those in which the photochemically oligomerizable or polymerizable mesogenic residues $A^1$, $A^2$ and $A^3$ are, independently, residues of the formula

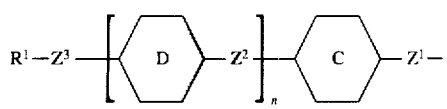

wherein

C and D are, independently, selected from the group consisting of pyridine-2,5-diyl, pyrimidine-2,5-dyl, trans-1,4-cyclohexylene, trans-1,3-dioxane-2,5-dyl and 1,4-phenylene, which phenylene may be substituted with one or more nitro, acetyl, halogen, methyl and cyano;

Z1 is selected from the group consisting of a single bond, —$CH_2CH_2$—, —$CH_2O$—, —COO—, —OOC—, —$(CH_2)_4$— and —$(CH_2)_3O$—;

$Z^2$ is selected from the group consisting of a single bond, —$CH_2CH_2$—, —$CH_2O$—, —$OCH_2$—, —COO—, —OOC—, —$(CH_2)_4$—, —$O(CH_2)_3$— and —$(CH_2)_3O$—;

$Z^3$ is selected from the group consisting of —$(CY_2)_m$—, —$(CY_2)_mO$—, —$(CY_2)_mCOO$—, —$(CY_2)_mOOC$, —$(Si[(CH_3)_2]O)_p$—, —$OCH_2(Si[(CH_3)_2]O)_pSi[(CH_3)_2]CH_2O$— and —$NHCH_2(Si[(CH_3)_2]O)_pSi[(CH_3)_2]CH_2NH$—;

Y is hydrogen or fluorine;

m is a whole number of 1 to 16;

p is a whole number of 1 to 16;

n is 0 or 1; and $R^1$ is a polymerizable group selected from the group consisting of acrylate, allyl ether, allyl ester, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative and fumaric acid derivative; or a dimerizable group selected from the group consisting of chalcone and a cinnamic acid derivative which may be substituted with one or more methyl, methoxy, cyano and halogen.

According to the present invention, preferred 1,4-phenylene which may be substituted with one or more nitro, acetyl, halogen, methyl and cyano include 1,4-phenylene, 2-nitro-1,4-phenylene, 3-nitro-1,4-phenylene, 2-acetyl-1,4-phenylene, 3-acetyl-1,4-phenylene, 2-fluoro-1,4-phenylene, 3-fluoro-1,4-phenylene, 2,3-difluoro-1,4-phenylene, 2-chloro-1,4-phenylene, 3-chloro-1,4-phenylene, 2,3-dichloro-1,4-phenylene, 2-cyano-1,4-phenylene, 3-cyano-1,4-phenylene, 2,3-dicyano-1,4-phenylene, 2-methyl-1,4-phenylene or 3-methyl-1,4-phenylene.

Compounds of formula I in which two of the mesogenic residues $A^1$, $A^2$ and $A^3$ are the same are preferred. These are compounds of the formulae

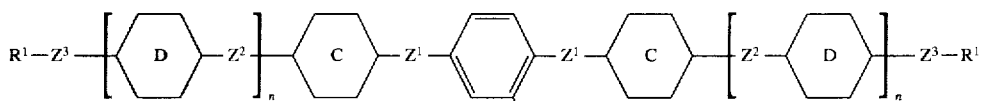

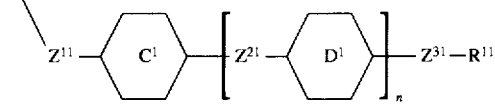

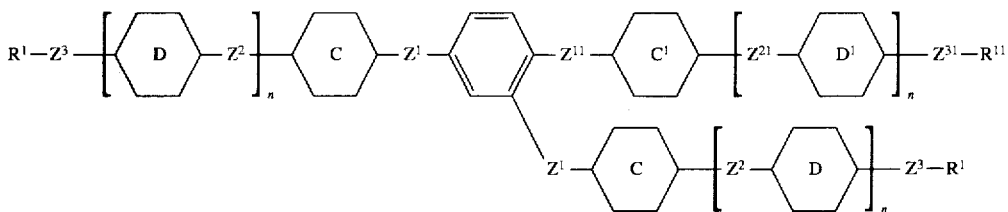

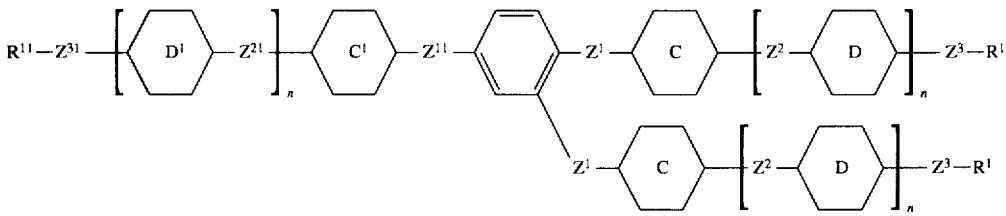

wherein

C, $C^1$, D and $D^1$ are, independently, selected from the group consisting of pyridine-2,5-diyl, pyrimidine-2,5-diyl, trans-1,4-cyclohexylene, trans-1,3-dioxane-2,5-diyl and 1,4-phenylene, which phenylene may be substituted with one-or more nitro, acetyl, halogen, methyl and cyano;

$Z^1$ and $Z^{11}$ are, independently, selected from the group consisting of a single bond, —$CH_2CH_2$—, —$CH_2O$—, —COO—, —OOC—, —$(CH_2)_4$— and —$(CH_2)_3O$—;

$Z^2$ and $Z^{21}$ are, independently, selected from the group consisting of a single bond, —$CH_2CH_2$—, —$CH_2O$—, —$OCH_2$—, —COO—, —OOC—, —$(CH_2)_4$—, —$O(CH_2)_3$— and —$(CH_2)_3O$—;

$Z^3$ and $Z^{31}$ are, independently, selected from the group consisting of —$(CY_2)_m$—, —$(CY_2)_mO$—, —$(CY_2)_mCOO$—, —$(CY_2)_mOOC$, —$(Si[(CH_3)_2]O)_p$—, —$OCH_2(Si[(CH_3)_2]O)_pSi[(CH_3)_2]CH_2O$— and —$NHCH_2(Si[(CH_3)_2]O)_pSi[(CH_3)_2]CH_2NH$—;

Y is hydrogen or fluorine;

m is a whole number of 1 to 16;

p is a whole number of 1 to 16;

n is 0 or 1; and $R^1$ and $R^{11}$ are, independently, a polymerizable group selected from the group consisting of acrylate, allyl ether, allyl ester, methacrylate, 2-chloro-acrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative and fumaric acid derivative; or a dimerizable group selected from the group consisting of chalcone and a cinnamic acid derivative which may be substituted with one or more methyl, methoxy, cyano and halogen.

Most particularly preferred compounds of formula I are those in which the mesogenic residues $A^1$, $A^2$ and $A^3$ are the same, and are compounds of the formula

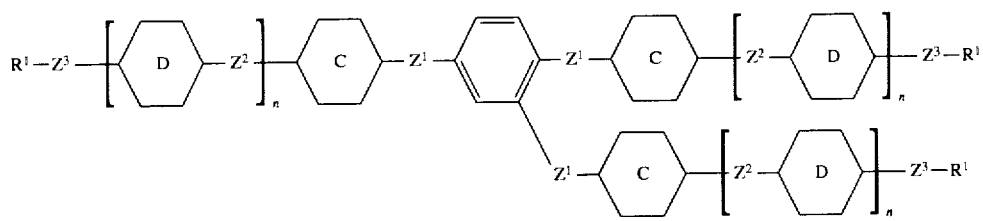

wherein $R^1$, $Z^3$, $Z^2$, $Z^1$ and n have the aforementioned significances.

The mesophase type of the compounds of the present invention can be influenced by varying the rings C or $C^1$ and D or $D^1$. Heterocyclic rings tend to produce smectic phases, while phenylene and cyclohexylene rings promote nematic tendencies. Preferably, rings C or $C^1$ and D or $D^1$ are, independently, selected from the group consisting of 1,4-phenylene, 2-fluoro-1,4-phenylene, 3-fluoro-1,4-phenylene, pyridine-2,5-diyl and pyrimidine-2,5-diyl, and especially preferred, are selected from the group consisting of 1,4-phenylene, 2-fluoro-1,4-phenylene and 3-fluoro-1,4-phenylene.

Especially preferred compounds of formulae I-1 to I-4 are compounds in which $Z^1$ and $Z^{11}$ are, independently, selected from the group consisting of —$CH_2O$—, —COO— and —OOC—; $Z^2$ and $Z^{21}$ are, independently, selected from the group consisting of a single bond, —$CH_2CH_2$—, —$CH_2$—, —$OCH_2$—, —COO— and —OOC—; and Y is hydrogen.

In especially preferred compounds of formulae I-1 to I-4 the residues $R^1$ and $R^{11}$ are, independently, acrylate, methacrylate, 2-chloroacrylate, 2-phenylacrylate, acryloylphenylene, acrylamide, methacrylamide, 2-phenylacrylamide, epoxy, vinyl ether, vinyl ester, styrene derivative, maleic acid derivative and fumaric acid derivative; acrylate, methacrylate, vinylether and epoxy are quite especially preferred.

In preferred compounds of formula I, the mesogenic residues $A^1$, $A^2$ and $A^3$ are a residue of formula II in which n=0, and the residues have the formula

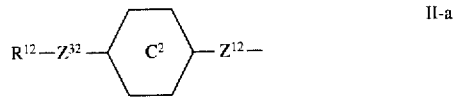

wherein $R^{12}$ is selected from the group consisting of acrylate, methacrylate and epoxy;

$Z^{32}$ is selected from the group consisting of —$(CH_2)_t$—, —$(CH_2)_tO$—, —$(CH_2)_tCOO$— and —$(CH_2)_tOOC$—; t is a whole number of 3 to 12;

$C^2$ is selected from the group consisting of 1,4-phenylene, 2-fluoro-1,4-phenylene and 3-fluoro-1,4-phenylene; and $Z^{12}$ is selected from the group consisting of —$CH_2O$—, —COO— and —OOC—.

Especially preferred compounds of formula I having residues $A^1$, $A^2$ and $A^3$ of formula II-a are

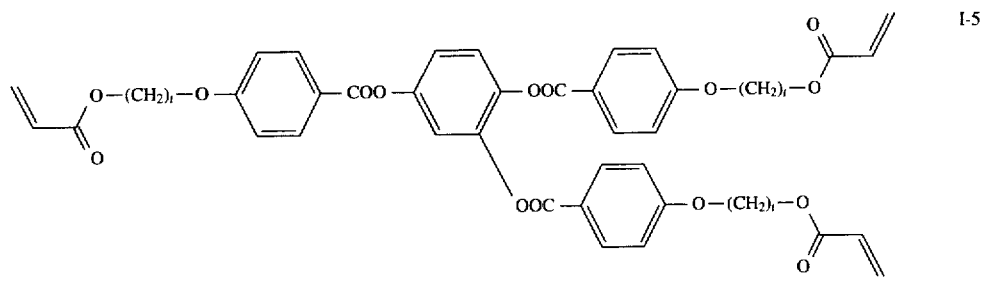

wherein t signifies a whole number of 3 to 12.

The compounds of the present invention having the general formulae I, I-1, I-2 and I-3, in which the mesogenic residues $A^1$, $A^2$ and $A^3$ are different from one another are very readily synthesized and can be produced according to known methods, for example analogously to the methods illustrated in Schemes 1 to 3 and in the Examples.

The mesogenic residues of formulae II and II-a are known or are analogs of known structures and can be prepared by known methods and subsequently linked with the aromatic ring.

A small mount of BHT (2,6-di-tert.-butyl-4-methyl-phenol="butylhydroxytoluene") is admixed in each step in order to stop undesired thermal cross-linking.

Scheme 1
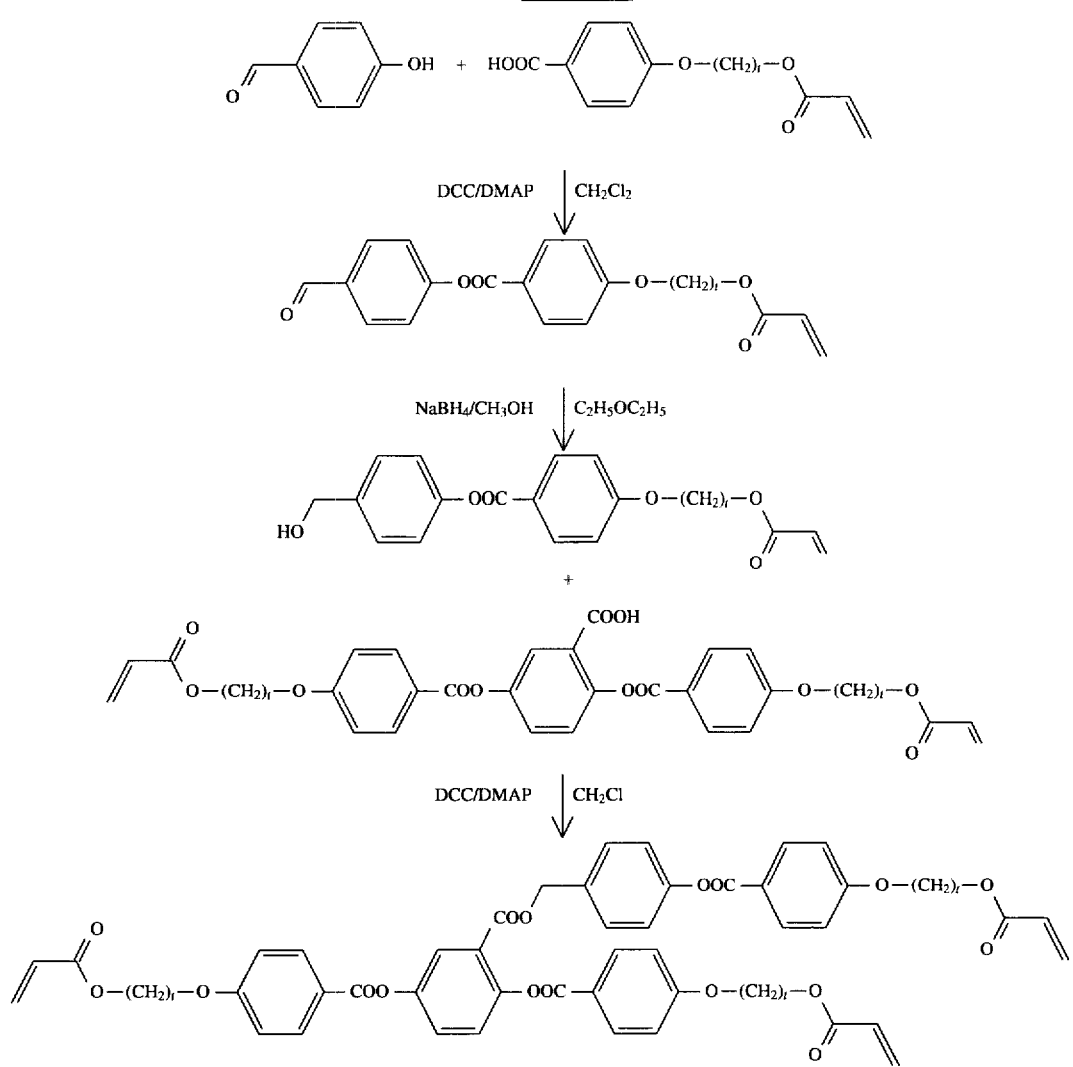
Scheme 2
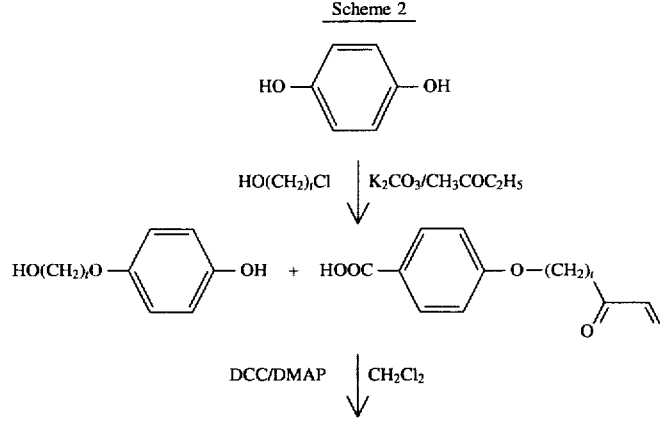

-continued
Scheme 2
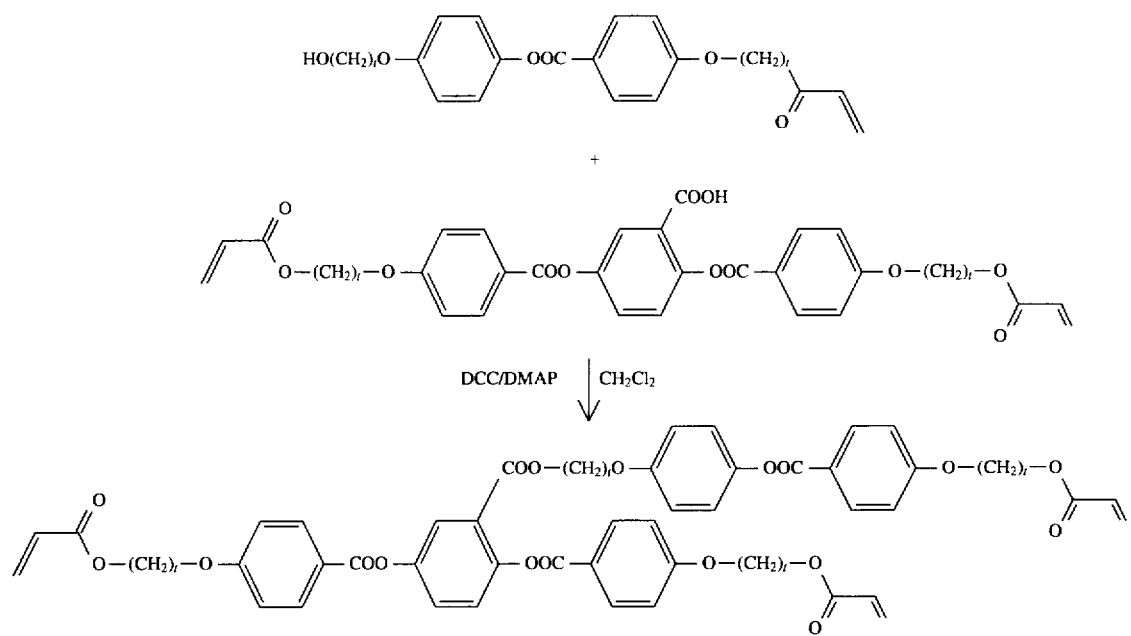
Scheme 3
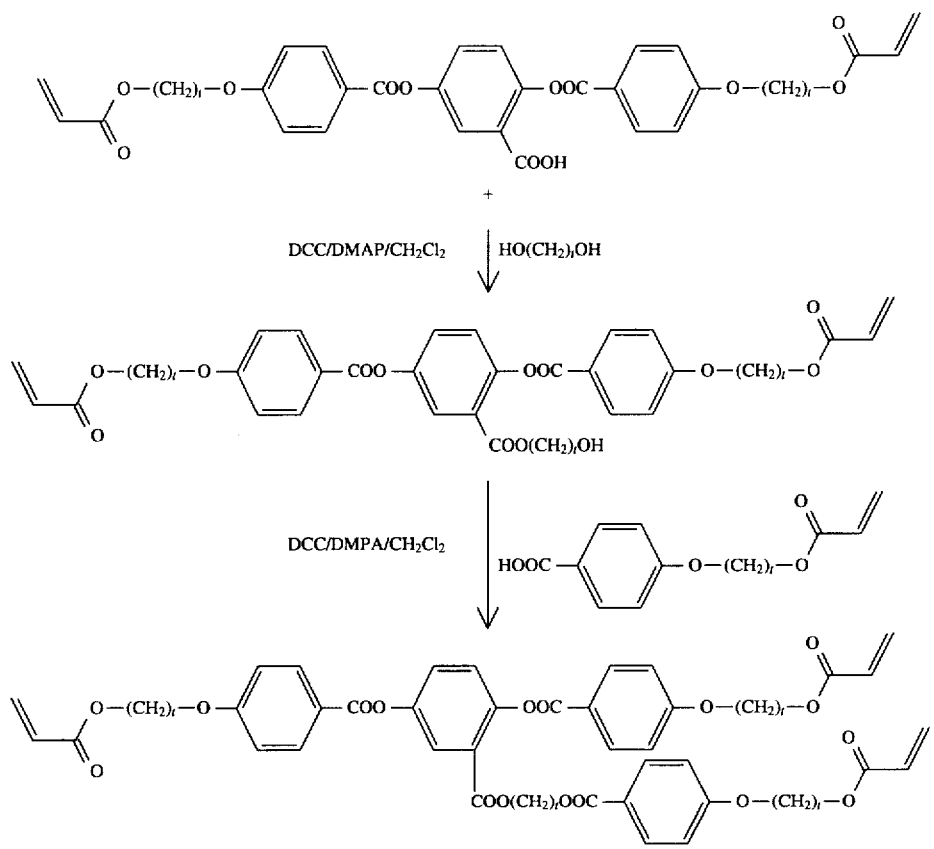

Compounds of formulae I-4 and I-5 in which the mesogenic residues $A^1$, $A^2$ and $A^3$ are the same can be produced by a simple and known method, for example, from 1,2,4-trihydroxyphenol and the corresponding acid derivatives of formula II such as 4-[n-acryloyloxyalkyloxy)]benzoic acids, as shown in Scheme 4. The esterification can be effected, for example, in the presence of N,N'-dicyclohexylcarbodiimide and 4-(dimethylamino)pyridine in dichloromethane or another suitable solvent such as chloroform.

The starting materials are known and are commercially available.

Scheme 4

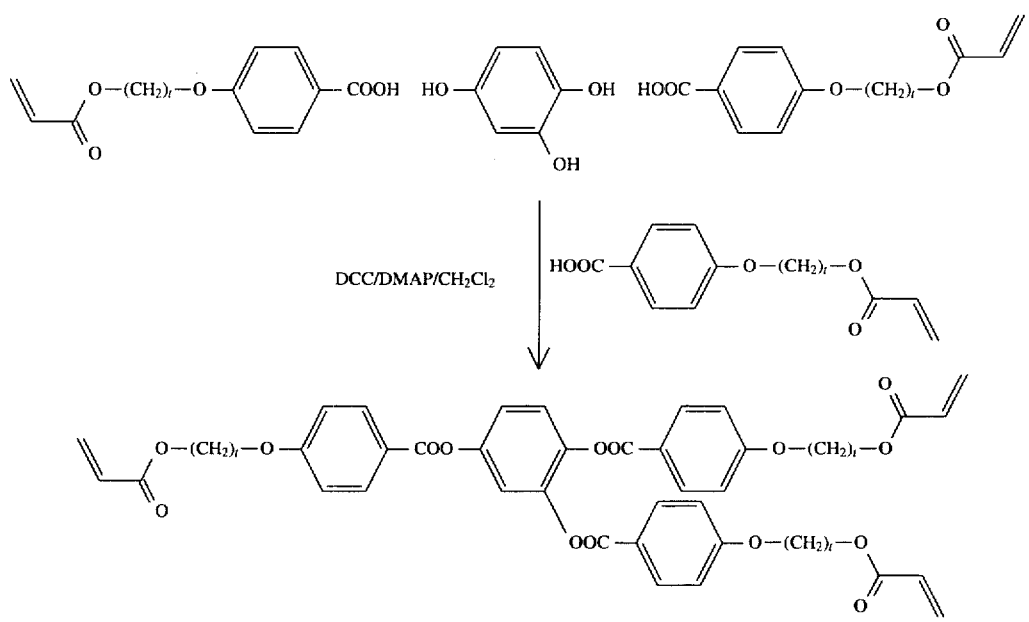

The compounds of formula I can be used as single compounds or in the form of mixtures with one another or with other liquid crystal components.

The liquid crystalline mixtures of the present invention contain at least two components, at least one of which component is a compound of formula I. A second component and any other additional components can comprise compounds of formula I or other known liquid crystal compounds with or without photo-crosslinkable groups. One or more chiral compounds can also be present in the mixture.

Due to the good solubility of the compounds of formula I and due to their good miscibility with one another, the content of different compounds of formula I in the liquid crystal mixtures of the present invention can be as high as 100 wt. %. Preferably, the mixtures in accordance with the present invention, in addition to one or more compounds of formula I, contain one or more compounds from the group of compounds of the general formulae as described in Swiss Patent Application CH 953/94:

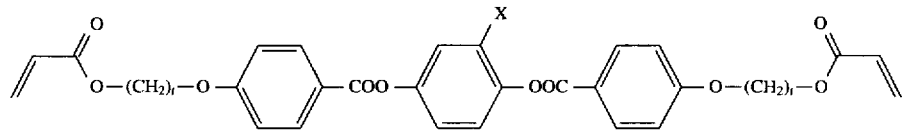

III

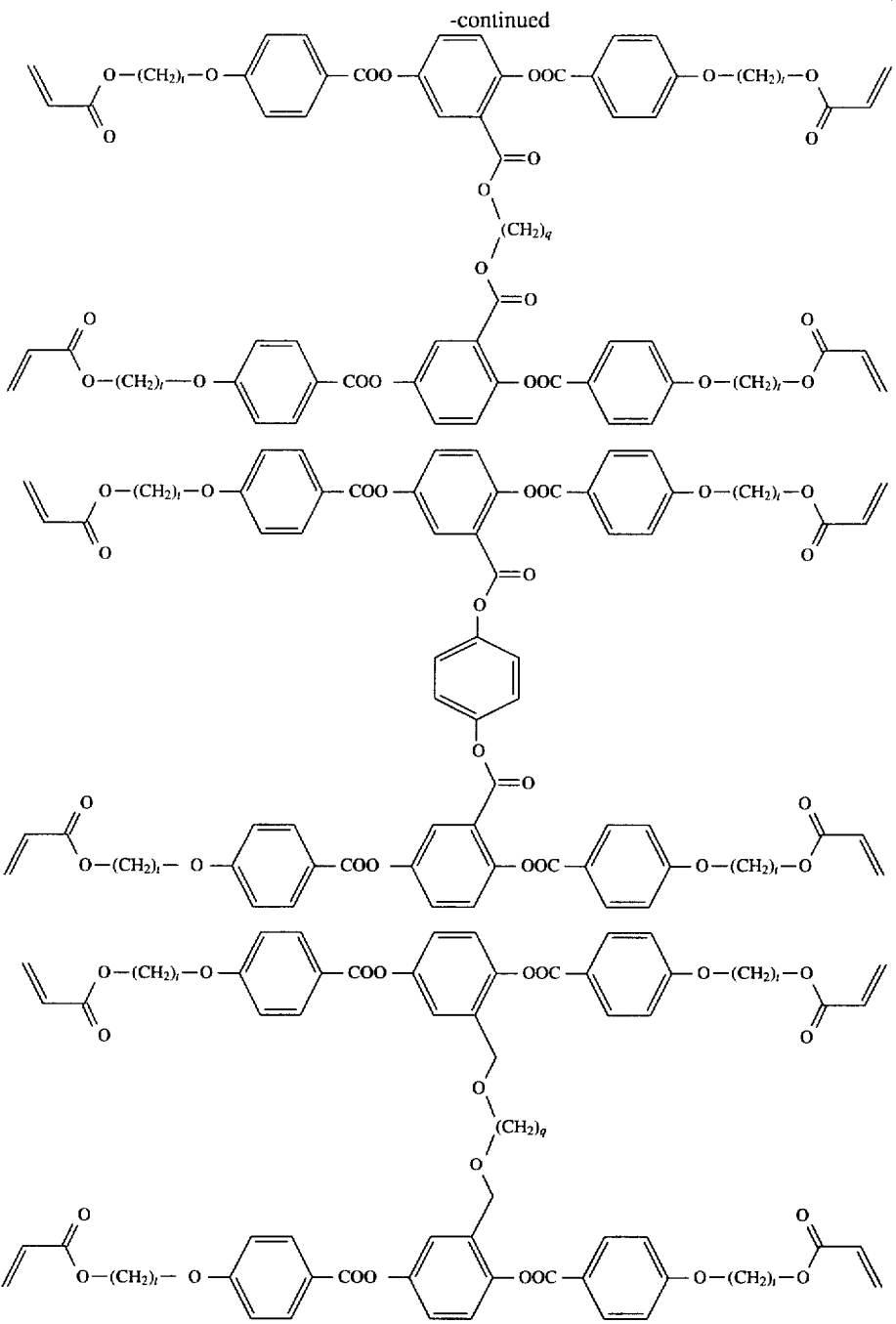

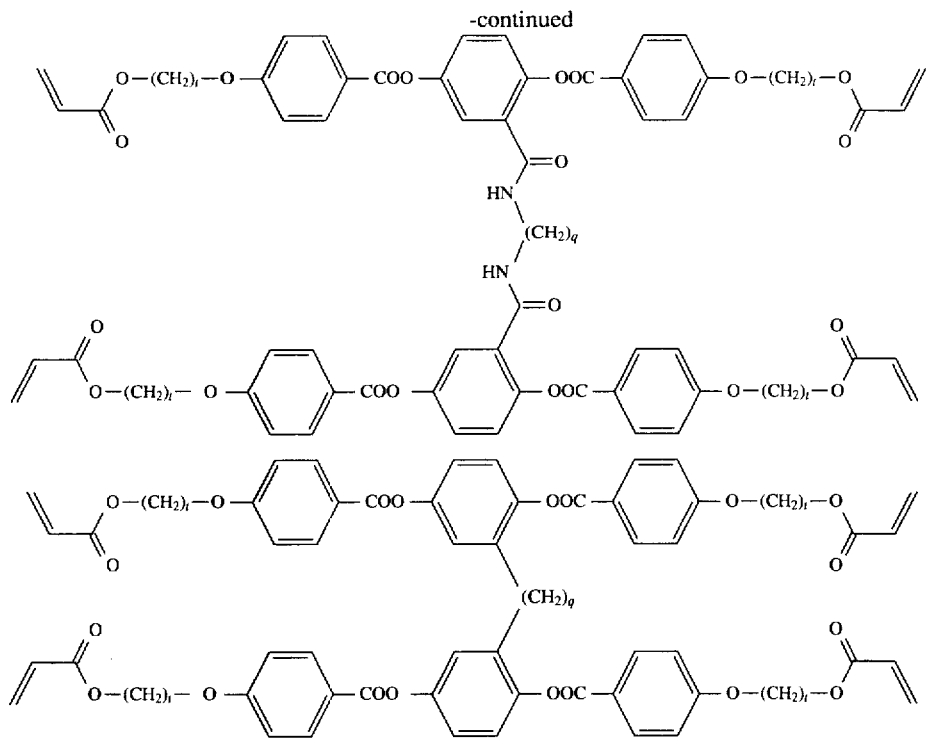

wherein t is a whole number of 3 to 12;

q is a whole number of 2 to 12; and

X is selected from the group consisting of hydrogen, fluorine, and chlorine; or lower alkyl such as methyl, ethyl, propyl or butyl.

The production of the compounds of formula I and of liquid crystalline mixtures containing compounds of Formula I are illustrated in more detail by the following Examples. C is a crystalline phase, S is a smectic phase, N is a nematic phase and I is the isotropic phase.

EXAMPLE 1

5.0 g of N,N'-dicyclohexylcarbodiimide were added at room temperature while stirring to a solution of 4.7 g of 4-[6-acryloyloxyhexyloxy]benzoic acid, 0.5 g of trihydroxybenzene and 0.2 g of 4-dimethylaminopyridine in 25 ml of dichloromethane. The reaction mixture was stirred at room temperature overnight, poured into 100 ml of water and then extracted three times with 50 ml of dichloromethane each time. The combined organic phases were washed twice with 100 ml of water each time, dried over magnesium sulphate, filtered and the filtrate was subsequently concentrated. Chromatographic purification of the residue on silica gel with hexane/ethyl acetate (vol. 3:1) and two-fold recrystallization from ethyl alcohol of the fractions which were pure according to thin-layer chromatography gave 2.0 g of 1,2,4-tri(4-[6-acryloyloxyhexyloxy]-phenylcarbonyloxy)-benzene; m.p. (C-I) 44° C., cl.p. (N-I) 33° C.

The following compounds were prepared in an analogous manner:

1,2,4-Tri(4-[3-acryloyloxypropyloxy]phenylcarbonyloxy) benzene;

1,2,4-tri(4-[4-acryloyloxybutyloxy]phenylcarbonyloxy) benzene; m.p. (C—I) 46° C., cl.p. (N—I) −8° C.;

1,2,4-tri(4-[5-acryloyloxypentyloxy]phenylcarbonyloxy) benzene; m.p. (C—I) 39° C., cl.p. (N—I) 33° C.;

1,2,4-tri(4-[7-acryloyloxyheptyloxy]phenylcarbonyloxy) benzene; m.p. (C—N) 31° C., cl.p. (N—I) 44° C.;

1,2,4-tri(4-[8-acryloyloxyoctyloxy]phenylcarbonyloxy)benzene; m.p. (C—I) 56° C., cl.p. (N—I) 42° C.;

1,2,4-tri(4-[9-acryloyloxynonyloxy]phenylcarbonyloxy) benzene; m.p. (C—N) 41° C., cl.p. (N—I) 51° C.;

1,2,4-tri(4-[10-acryloyloxydecyloxy]phenylcarbonyloxy) benzene; m.p. (C—I) 55° C.; cl.p. (N—I) 46° C.;

1,2,4-tri(4-[11-acryloyloxyundecyloxy]phenylcarbonyloxy) benzene; m.p. (C—N) 44° C.; cl.p. (N—I) 53° C.

EXAMPLE 2

0.2 g of N,N'-dicyclohexylcarbodiimide is added at room temperature while stirring to a solution of 0.6 g of 2,5-bis(4-[6-acryloyloxyhexyloxy]-phenylcarbonyloxy)-benzoic acid, 0.4 g [4-(4-[6-acryloyloxyhexyloxy]-phenylcarbonyloxy)phenyl]methanol and 0.04 g of 4-dimethylaminopyridine in 20 ml of dichloromethane. The reaction mixture is stirred at room temperature overnight, poured into 100 ml of water and then extracted three times with 50 ml of dichloromethane each time. The combined organic phases are washed twice with 100 ml of water each time, dried over magnesium sulphate, filtered and the filtrate is subsequently concentrated. Chromatographic purification of the residue on silica gel with hexane/ethyl acetate (vol. 1:1) and two-fold recrystallization from acetone of the fractions which are pure according to thin-layer chromatography gives 0.4 g of [4-(4-[6-acryloyloxyhexyloxy]-phenylcarbonyloxy)-phenyl]-methyl 2,5-bis(4-[6-acryloyloxyhexyloxy]-phenylcarbonyloxy)-benzoate.

The [4-(4-[6-acryloyloxyhexyloxy]-phenylcarbonyloxy)phenyl]-methanol used as the starting material is prepared as follows:

(a) 0.6 g of N,N'-dicyclodicyclohexylcarbodiimide is added at room temperature while stirring to a solution of 1.0 g of 4-[6-acryloyloxyhexyloxy]benzoic acid, 0.3 g of 4-hydroxybenzaldehyde and 0.04 g of 4-dimethylaminopyridine in 20 ml of dichloromethane. The reaction mixture is stirred at room temperature overnight, poured into 100 ml of water and then extracted three times with 50 ml of dichloromethane each time. The combined organic phases are washed twice with 100 ml of water each time, dried over magnesium sulphate, filtered and the filtrate is subsequently concentrated. Chromatographic purification of the residue on silica gel with hexane/ethyl acetate (vol. 1:1) and twofold recrystallization from ethanol of the fractions which are pure according to thin-layer chromatography gives 0.9 g of 4-(4-[6-acryloyloxyhexyloxy]phenylcarbonyloxy)benzaldehyde.

(b) A mixture of 0.13 g of sodium borohydride and 15 ml of water is treated dropwise at 0° C. with a solution of 0.8 g of 4-(4-[6-acryloyloxyhexyloxy]phenylcarbonyloxy)benzaldehyde in 100 ml of dioxan. The reaction mixture is stirred at 0° C. for a further 60 minutes and then at room temperature for 10 minutes, poured into 100 ml of dichloromethane and washed twice with 100 ml of water each time. The combined aqueous phases are extracted twice with 50 ml of dichloromethane each time. The combined organic phases are then washed twice with 100 ml of water each time, dried over magnesium sulphate, the suspension is filtered and the filtrate is concentrated. The residue is used in the next step without further purification.

The following compounds can be prepared in an analogous manner:

[4-(4-[6-Acryloyloxyhexyloxy]phenylcarbonyloxy)phenyl] methyl 2,5-bis(4-[7-acryloyloxyheptyloxy]phenylcarbonyloxy)benzoate;

[4-(4-[6-acryloyloxyhexyloxy]phenylcarbonyloxy)phenyl] methyl 2,5-bis(4-[8-acryloyloxyoctyloxy]phenylcarbonyloxy)benzoate;

[4-(4-[6-acryloyloxyhexyloxy]phenylcarbonyloxy)phenyl] methyl 2,5-bis(4-[9-acryloyloxynonyloxy]phenylcarbonyloxy)benzoate;

[4-(4-[6-acryloyloxyhexyloxy]phenylcarbonyloxy)phenyl] methyl 2,5-bis(4-[10-acryloyloxydecyloxy]phenylcarbonyloxy)benzoate;

[4-(4-[6-acryloyloxyhexyloxy]phenylcarbonyloxy)phenyl] methyl 2,5-bis(4-[11-acryloyloxyundecyloxy]phenylcarbonyloxy)benzoate;

[4-(4-[6-acryloyloxyhexyloxy]phenylcarbonyloxy)phenyl] methyl 2,5-bis(4-[12-acryloyloxydodecyloxy]phenylcarbonyloxy)benzoate;

[4-(4-[3-acryloyloxypropyloxy]phenylcarbonyloxy)phenyl] methyl 2,5-bis(4-[7-acryloyloxyheptyloxy]phenylcarbonyloxy)benzoate;

[4-(4-[4-acryloyloxybutyloxy]phenylcarbonyloxy)phenyl] methyl 2,5-bis(4-[8-acryloyloxyoctyloxy]phenylcarbonyloxy)benzoate;

[4-(4-[5-acryloyloxypentyloxy]phenylcarbonyloxy)phenyl] methyl 2,5-bis(4-[9-acryloyloxynonyloxy]phenylcarbonyloxy)benzoate;

[4-(4-[7-acryloyloxyheptyloxy]phenylcarbonyloxy)phenyl] methyl 2,5-bis(4-[10-acryloyloxydecyloxy]phenylcarbonyloxy)benzoate;

[4-(4-[8-acryloyloxyoctyloxy]phenylcarbonyloxy)phenyl] methyl 2,5-bis(4-[12-acryloyloxydodecyloxy]phenylcarbonyloxy)benzoate;

[4-(4-[9-acryloyloxynonyloxy]phenylcarbonyloxy)phenyl] methyl 2,5-bis(4-[11-acryloyloxyundecyloxy]phenylcarbonyloxy)benzoate;

[4-(4-[10-acryloyloxydecyloxy]phenylcarbonyloxy)phenyl] methyl 2,5-bis(4-[11-acryloyloxyundecyloxy]phenylcarbonyloxy)benzoate;

[4-(4-[11-acryloyloxyundecyloxy]phenylcarbonyloxy)phenyl]methyl 2,5-bis(4-[11-acryloyloxyundecyloxy]phenylcarbonyloxy)benzoate;

[4-(4-[12-acryloyloxydodecyloxy]phenylcarbonyloxy)phenyl]methyl 2,5-bis(4-[12-acryloyloxydodecyloxy]phenylcarbonyloxy)benzoate.

EXAMPLE 3

0.6 g of 2,5-bis(4-[6-acryloyloxyhexyloxy]phenylcarbonyloxy)benzoic acid, 0.4 g of [4-(4-[6-acryloyloxyhexyloxy]phenylcarbonyloxy)-phenoxy]ethanol, 0.04 g of 4-dimethylaminopyridine and 0.2 g of N,N'-dicyclodicyclohexylcarbodiimide in 20 ml of dichlormethane are reacted in an analogous manner to Example 1 to give [4-(4-[6-acryloyloxyhexyloxy]phenylcarbonyloxy)phenoxy]ethyl 2,5-bis(4-[6-acryloyloxyhexyloxy)]phenylcarbonyloxy)benzoate.

The [4-(4-[6-acryloyloxyhexyloxy]phenylcarbonyloxy)phenoxy]ethanol used as the starting material is prepared as follows:

(a) 0.6 g of 4-[6-acryloyloxyhexyloxy)]benzoic acid, 0.2 g of (4-hydroxyphenoxy)ethanol, 0.04 g of 4-dimethylaminopyridine and 0.4 g of N,N'-dicyclodicyclohexylcarbodiimide in 50 ml of dichloromethane are reacted in an analogous manner to Example 1 to give 0.4 g of [4-(4-[6-acryloyloxyhexyloxy]phenylcarbonyloxy)phenoxy]ethanol.

The following compounds can be prepared in an analogous manner:

[4-(4-[6-Acryloyloxyhexyloxy]phenylcarbonyloxy)phenoxy]ethyl 2,5-bis(4-[3-acryloyloxypropyloxy]phenylcarbonyloxy)benzoate;

[4-(4-[6-acryloyloxyhexyloxy]phenylcarbonyloxy)phenoxy]ethyl 2,5-bis(4-[4-acryloyloxybutyloxy]phenylcarbonyloxy)benzoate;

[4-(4-[6-acryloyloxyhexyloxy]phenylcarbonyloxy)phenoxy]ethyl 2,5-bis(4-[5-acryloyloxypentyloxy]phenylcarbonyloxy)benzoate;

[4-(4-[6-acryloyloxyhexyloxy]phenylcarbonyloxy)phenoxy]ethyl 2,5-bis(4-[7-acryloyloxyheptyloxy]phenylcarbonyloxy)benzoate;

[4-(4-[6-acryloyloxyhexyloxy]phenylcarbonyloxy)phenoxy]ethyl 2,5-bis(4-[8-acryloyloxyoctyloxy]phenylcarbonyloxy)benzoate;

[4-(4-[6-acryloyloxyhexyloxy]phenylcarbonyloxy)phenoxy]ethyl 2,5-bis(4-[9-acryloyloxynonyloxy]phenylcarbonyloxy)benzoate;

[4-(4-[6-acryloyloxyhexyloxy]phenylcarbonyloxy)phenoxy]ethyl 2,5-bis(4-[10-acryloyloxydecyloxy]phenylcarbonyloxy)benzoate;

[4-(4-[6-acryloyloxyhexyloxy]phenylcarbonyloxy)phenoxy]ethyl 2,5-bis(4-[11-acryloyloxyundecyloxy]phenylcarbonyloxy)benzoate;

[4-(4-[6-acryloyloxyhexyloxy]phenylcarbonyloxy)phenoxy]ethyl 2,5-bis(4-[12-acryloyloxydodecyloxy]phenylcarbonyloxy)benzoate;

[4-(4-[6-acryloyloxyhexyloxy]phenylcarbonyloxy)phenoxy]propyl 2,5-bis(4-[7-acryloyloxyheptyloxy]phenylcarbonyloxy)benzoate;

[4-(4-[6-acryloyloxyhexyloxy]phenylcarbonyloxy)phenoxy]butyl 2,5-bis(4-[8-acryloyloxyoctyloxy]phenylcarbonyloxy)benzoate;

[4-(4-[6-acryloyloxyhexyloxy]phenylcarbonyloxy)phenoxy]pentyl 2,5-bis(4-[9-acryloyloxynonyloxy]phenylcarbonyloxy)benzoate;

[4-(4-[6-acryloyloxyhexyloxy]phenylcarbonyloxy)phenoxy]hexyl 2,5-bis(4-[10-acryloyloxydecyloxy]phenylcarbonyloxy)benzoate;

[4-(4-[6-acryloyloxyhexyloxy]phenylcarbonyloxy)phenoxy]heptyl 2,5-bis(4-[11-acryloyloxyundecyloxy]phenylcarbonyloxy)benzoate;

[4-(4-[6-acryloyloxyhexyloxy]phenylcarbonyloxy)phenoxy]octyl 2,5-bis(4-[-12-acryloyloxydodecyloxy]phenylcarbonyloxy)benzoate.

EXAMPLE 4

0.3 g of 4-[6-acryloyloxyhexyloxy]benzoic acid, 0.8 g of 4-hydroxybutyl 2,5-bis(4-[11-acryloyloxyundecyloxy]phenylcarbonyloxy)benzoate, 0.04 g of 4-dimethylaminopyridine and 0.2 g of N,N'-dicyclodicyclohexylcarbodiimide in 50 ml of dichloromethane are reacted in an analogous manner to Example 1 to give 0.5 g of 4-(4-[6-acryloyloxyhexyloxy]phenylcarbonyloxy)butyl 2,5-bis(4-[11-acryloyloxyundecyloxy)]phenylcarbonyloxy)benzoate.

The following compounds can be prepared in an analogous manner:

3-(4-[6-Acryloyloxyhexyloxy]phenylcarbonyloxy)propyl 2,5-bis(4-[11-acryloyloxyundecyloxy]phenylcarbonyloxy)benzoate;

5-(4-[6-acryloyloxyhexyloxy]phenylcarbonyloxy)pentyl 2,5-bis(4-[11-acryloyloxyundecyloxy]phenylcarbonyloxy)benzoate;

6-(4-[6-acryloyloxyhexyloxy]phenylcarbonyloxy)hexyl 2,5-bis(4-[11-acryloyloxyundecyloxy]phenylcarbonyloxy)benzoate;

7-(4-[6-acryloyloxyhexyloxy]phenylcarbonyloxy)heptyl 2,5-bis(4-[11-acryloyloxyundecyloxy]phenylcarbonyloxy)benzoate;

8-(4-[6-acryloyloxyhexyloxy]phenylcarbonyloxy)octyl 2,5-bis(4-[11-acryloyloxyundecyloxy]phenylcarbonyloxy)benzoate;

9-(4-[6-acryloyloxyhexyloxy]phenylcarbonyloxy)nonyl 2,5-bis(4-[11-acryloyloxyundecyloxy]phenylcarbonyloxy)benzoate;

10-(4-[6-acryloyloxyhexyloxy]phenylcarbonyloxy)decyl 2,5-bis(4-[11-acryloyloxyundecyloxy]phenylcarbonyloxy)benzoate;

11-(4-[6-acryloyloxyhexyloxy]phenylcarbonyloxy)undecyl 2,5-bis(4-[11-acryloyloxyundecyloxy]phenylcarbonyloxy)benzoate;

12-(4-[6-acryloyloxyhexyloxy]phenylcarbonyloxy)dodecyl 2,5-bis(4-[11-acryloyloxyundecyloxy]phenylcarbonyloxy)benzoate;

3-(4-[6-acryloyloxyhexyloxy]phenylcarbonyloxy)propyl 2,5-bis(4-[5-acryloyloxypentyloxy]phenylcarbonyloxy)benzoate;

3-(4-[6-acryloyloxyhexyloxy]phenylcarbonyloxy)propyl 2,5-bis(4-[6-acryloyloxyhexyloxy]phenylcarbonyloxy)benzoate;

3-(4-[6-acryloyloxyhexyloxy]phenylcarbonyloxy)propyl 2,5-bis(4-[7-acryloyloxyheptyloxy]phenylcarbonyloxy)benzoate;

3-(4-[6-acryloyloxyhexyloxy]phenylcarbonyloxy)propyl 2,5-bis(4-[8-acryloyloxyoctyloxy]phenylcarbonyloxy)benzoate;

3-(4-[6-acryloyloxyhexyloxy]phenylcarbonyloxy)propyl 2,5-bis(4-[9-acryloyloxynonyloxy]phenylcarbonyloxy)benzoate;

3-(4-[6-acryloyloxyhexyloxy]phenylcarbonyloxy)propyl 2,5-bis(4-[10-acryloyloxydecyloxy]phenylcarbonyloxy)benzoate.

EXAMPLE 5

A mixture (C—N, <20° C., N-I, 38° C.) of 80 wt. % 1,2,4-tri(4-[6-acryloyloxyhexyloxy]phenylcarbonyloxy)benzene and 20 wt. % 1-chloro-2,5-bis(4-[6-acryloyloxyhexyloxy)]phenylcarbonyloxy)benzene was treated with 1 wt. % of a photoinitiator (IRGACURE, Ciba Geigy), dissolved in anisole (40 wt. %) and then spun at 2000 revolutions per minute on to a glass plate. The glass plate had previously been coated with methacryloyloxyethyl 3-(E)-[4-cyano4'-biphenyl]acrylate and then irradiated with linear polarized light. Thereby, a predetermined structure was inscribed photolithographically by means of a mask in the photoorientable polymer network layer (PPN layer). The spun-on new layer (on the PPN layer) was dried at 90° C. on a heating block, then irradiated with xenon light in a vacuum oven under a vacuum at 90° C. The inscribed original structure remained and was copied faithfully by the new network. A clear double refraction (Dn) was recognizable. This layer functions as a structural optical retarder.

We claim:

1. Compounds of the general formula

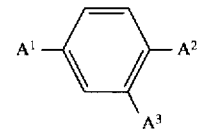

wherein $A^1$, $A^2$ and $A^3$ are, independently, photochemically polymerizable mesogenic residues of the formula

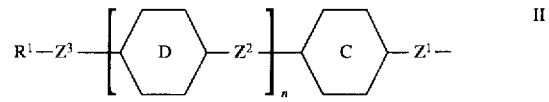

wherein

C and D are, independently selected from the group consisting of pyridine-2,5-diyl, pyrimidine-2,5-diyl, trans-1,4-cyclohexylene, trans-1,3-dioxane-2,5-diyl and 1,4-phenylene, which phenylene may be substituted with one or more nitro, acetyl, halogen, methyl and cyano;

$Z^1$ is selected from the group consisting of a single bond, —CH$_2$CH$_2$—, —CH$_2$O—, —COO—, —OOC—, —(CH$_2$)$_4$— and —(CH$_2$)$_3$O—;

$Z^2$ is selected from the group consisting of a single bond, —CH$_2$CH$_2$—, —CH$_2$O—, —OCH$_2$—, —COO—, —OOC—, —(CH$_2$)$_4$—, —O(CH$_2$)$_3$— and —(CH$_2$)$_3$O—;

$Z^3$ is selected from the group consisting of —(CY$_2$)$_m$—, —(CY$_2$)$_m$O—, —(CY$_2$)$_m$COO—, —(CY$_2$)$_m$OOC, —(Si[(CH$_3$)$_2$]O)$_p$—, —OCH$_2$(Si[(CH$_3$)$_2$]O)$_p$Si[(CH$_3$)$_2$]CH$_2$O— and —NHCH$_2$(Si[(CH$_3$)$_2$]O)$_p$Si[(CH$_3$)$_2$]CH$_2$NH—;

Y is hydrogen or fluorine;

m is a whole number of 1 to 16;

p is a whole number of 1 to 16;

n is 0 or 1; and $R^1$ is a polymerizable group selected from the group consisting of acrylate, methacrylate, epoxy and vinyl ether.

2. The compounds of claim 1 wherein two of the mesogenic residues $A^1$, $A^2$ and $A^3$ are the same.

3. The compounds of claim 2 having the formulae

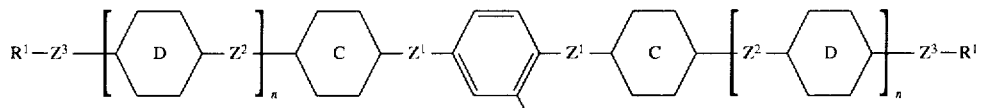

I-1

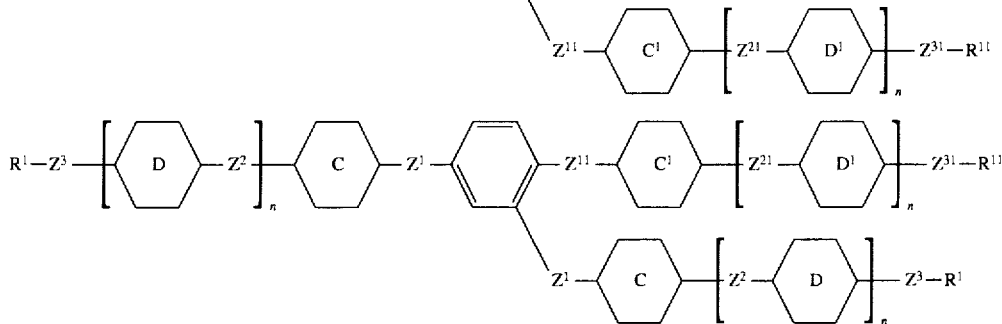

I-2

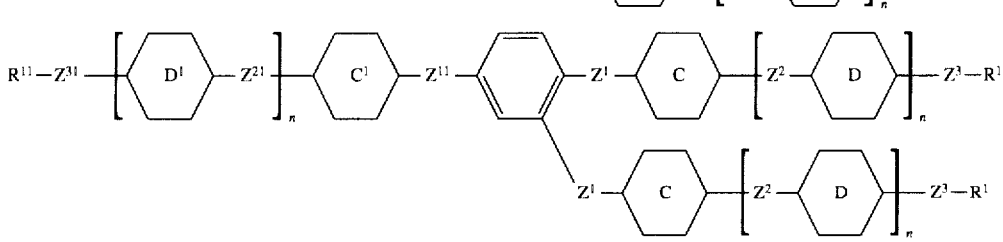

I-3 wherein

C, C¹ D and D¹ are, independently, selected from the group consisting of pyridine-2,5-diyl, pyrimidine-2,5-diyl, trans-1,4-cyclohexylene, trans-1,3-dioxane-2,5-diyl and 1,4-phenylene, which phenylene may be substituted with one or more nitro, acetyl, halogen, methyl and cyano;

$Z^1$ and $Z^{11}$ are, independently selected from the group consisting of a single bond, —CH$_2$CH$_2$—, —CH$_2$O—, —COO—, —OOC—, —(CH$_2$)$_4$— and —(CH$_2$)$_3$—;

$Z^2$ and $Z^{21}$ are, independently, selected from the group consisting of a single bond, —CH$_2$CH$_2$—, —CH$_2$O—, —OCH$_2$—, —COO—, —OOC—, —(CH$_2$)$_4$—, —O(CH$_2$)$_3$— and —(CH$_2$)$_3$O—;

$Z^3$ and $Z^{31}$ are, independently, selected from the group consisting of —(CY$_2$)$_m$—, —(CY$_2$)$_m$O—, —(CY$_2$)$_m$COO—, —(CY$_2$)$_m$OOC, —(Si[(CH$_3$)$_2$]O)$_p$—, —OCH$_2$(Si[(CH$_3$)$_2$]O)$_p$Si[(CH$_3$)$_2$]CH$_2$O— and —NHCH$_2$(Si[(CH$_3$)$_2$]O)$_p$Si[(CH$_3$)$_2$]CH$_2$NH—;

Y is hydrogen or fluorine;

m is a whole number of 1 to 16;

p is a whole number of 1 to 16;

n is 0 or 1; and $R^1$ and $R^{11}$ are, independently, a polymerizable group selected from the group consisting of acrylate, methacrylate, epoxy and vinyl ether.

4. The compounds of claim 1 wherein the mesogenic residues $A^1$, $A^2$ and $A^3$ are the same, having the formula

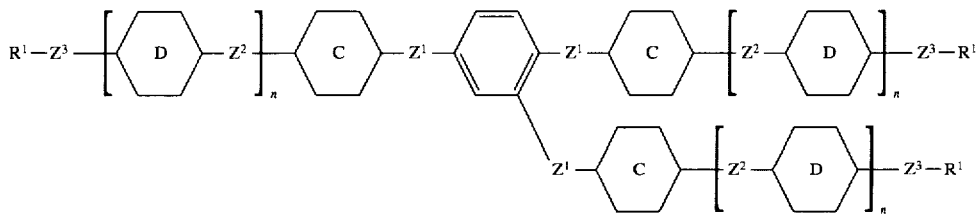

I-4 wherein

C and D are, independently selected from the group consisting of pyridine-2,5-diyl, pyrimidine-2,5-diyl, trans-1,4-cyclohexylene, trans-1,3-dioxane-2,5-diyl and 1,4-phenylene, which phenylene may be substituted with one or more nitro, acetyl, halogen, methyl and cyano;

$Z^1$ is selected from the group consisting of a single bond, —CH$_2$CH$_2$—, —CH$_2$O—, —COO—, —OOC—, —(CH$_2$)$_4$— and —(CH$_2$)$_3$O—;

$Z^2$ is selected from the group consisting of a single bond, —CH$_2$CH$_2$—, —CH$_2$O—, —OCH$_2$—, —COO—, —OOC—, —(CH$_2$)$_4$—, —O(CH$_2$)$_3$— and —(CH$_2$)$_3$O—;

$Z^3$ is selected from the group consisting of —(CY$_2$)$_m$—, —(CY$_2$)$_m$O—, —(CY$_2$)$_m$COO—, —(CY$_2$)$_m$OOC, —(Si[(CH$_3$)$_2$]O)$_p$—, —OCH$_2$(Si[(CH$_3$)$_2$]O)$_p$Si[(CH$_3$)$_2$]CH$_2$O— and —NHCH$_2$(Si[(CH$_3$)$_2$]O)$_p$Si[(CH$_3$)$_2$]CH$_2$NH—;

Y is hydrogen or fluorine;

m is a whole number of 1 to 16;

p is a whole number of 1 to 16;

n is 0 or 1; and $R^1$ is a polymerizable group selected from the group consisting of acrylate, methacrylate, epoxy and vinyl ether.

5. The compounds of claim 3, wherein $Z^1$ and, $Z^{11}$ are, independently, selected from the group consisting of —$CH_2O$—, —COO— and —OOC—; $Z^2$ and $Z^{21}$ are, independently, selected from the group consisting of a single bond, —$CH_2CH_2$, —$CH_2O$—, —$OCH_2$—, —COO— and —OOC—; and Y is hydrogen.

6. The compounds of claim 1 wherein the mesogenic residues $A^1$, $A^2$ and $A^3$ are each a residue of the formula

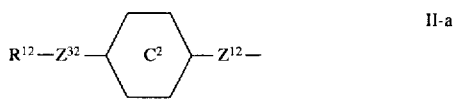
II-a wherein $R^{12}$ is selected from the group consisting of acrylate, methacrylate and epoxy;

$Z^{32}$ is selected from the group consisting of —$(CH_2)_t$—, —$(CH_2)_tO$—, —$(CH_2)_tCOO$— and —$(CH_2)_tOOC$—;

t is a whole number of 3 to 12;

$C^2$ is selected from the group consisting of 1,4-phenylene, 2-fluoro-1,4-phenylene and 3-fluoro-1,4-phenylene; and $Z^{12}$ is selected from the group consisting of $CH_2O$—, —COO— and —OOC—.

7. The compounds of claim 6 of the formula

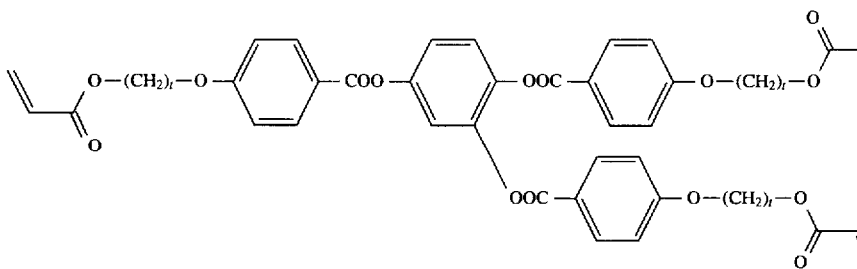
I-5 wherein t is a whole number of 3 to 12.

8. The compound of claim 7 which is 1,2,4-tri(4-[6-acryloyloxyhexyloxy]-phenylcarbonyloxy)benzene.

9. The compounds of claim 3, which is [4-(4-[6-acryloyloxyhexyloxy]-phenylcarbonyloxy)-phenyl]-methyl 2,5-bis(4-[6-acryloyloxyhexyloxy]phenylcarbonyloxy)benzoate.

10. The compound of claim 3, which is [4-(4-[6-acryloyloxyhexyloxy]phenylcarbonyloxy)-phenoxy]ethyl 2,5-bis(4-[6-acryloyloxyhexyloxy]phenylcarbonyloxy)benzoate.

11. The compound of claim 3, which is 4-(4-[6-acryloyloxyhexyloxy]phenylcarbonyloxy)butyl 2,5-bis(4-[11-acryloyloxyundecyloxy)]phenylcarbonyloxy)benzoate.

12. A polymerizable, liquid crystalline mixture comprising at least two components, wherein at least one component is a compound of formula

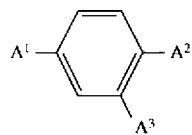
I wherein $A^1$, $A^2$ and $A^3$ are, independently, photochemically polymerizable mesogenic residues of the formula

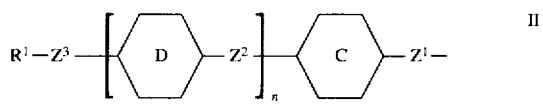
II wherein

C and D are, independently selected from the group consisting of pyridine-2,5-diyl, pyrimidine-2,5-diyl, trans-1,4-cyclohexylene, trans-1,3-dioxane-2,5-diyl and 1,4-phenylene, which phenylene may be substituted with one or more nitro, acetyl, halogen, methyl and cyano;

$Z^1$ is selected from the group consisting of a single bond, —$CH_2CH_2$—, —$CH_2O$—, —COO—, —OOC—, —$(CH_2)_4$— and —$(CH_2)_3O$—;

$Z^2$ is selected from the group consisting of a single bond, —$CH_2CH_2$—, —$CH_2O$—, —$OCH_2$—, —COO—, —OOC—, —$(CH_2)_4$—, —$O(CH_2)_3$— and —$(CH_2)_3O$—;

$Z^3$ is selected from the group consisting of —$(CY_2)_m$—, —$(CY_2)_mO$—, —$(CY_2)_mCOO$—, —$(CY_2)_mOOC$, —$(Si[(CH_3)_2]O)_p$—, —$OCH_2(Si[(CH_3)_2]O)_pSi[(CH_3)_2]CH_2O$— and —$NHCH_2(Si[(CH_3)_2]O)_pSi[(CH_3)_2]CH_2NH$—;

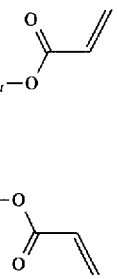

Y is hydrogen or fluorine;

m is a whole number of 1 to 16;

p is a whole number of 1 to 16;

n is 0 or 1; and $R^1$ is a polymerizable group selected from the group consisting of acrylate, methacrylate, epoxy and vinyl ether.

13. The polymerizable, liquid crystalline mixture of claim 12, which contains at least one compound of formula I, and at least one compound selected from the group of compounds comprising the formulae:

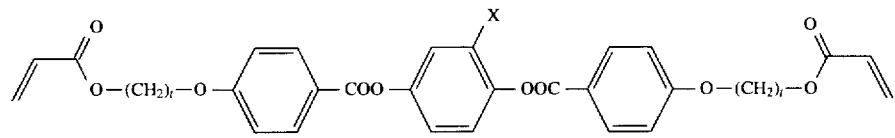
III
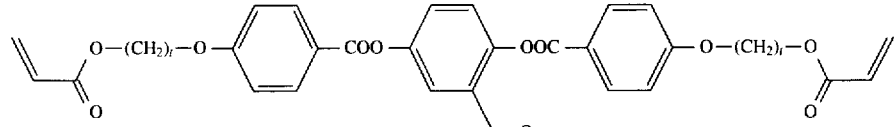
IV
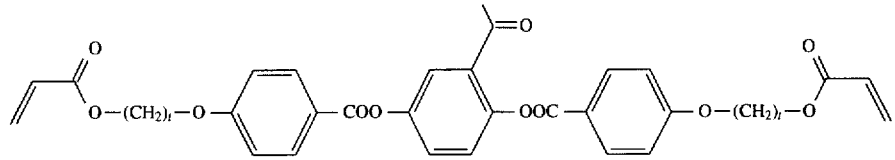
V
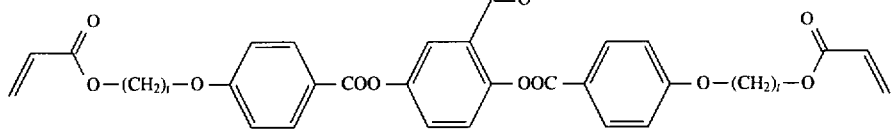
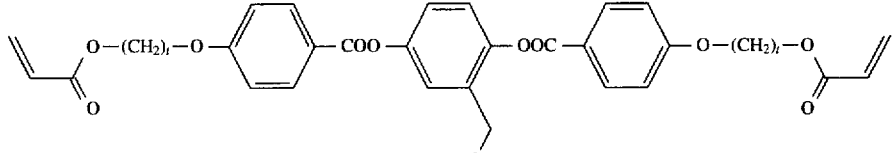
VI
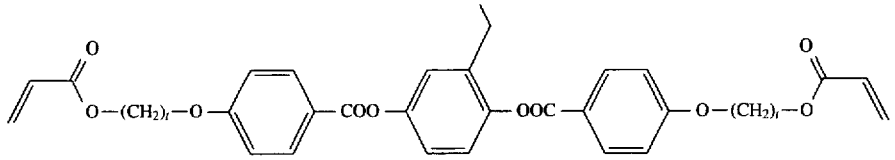

-continued
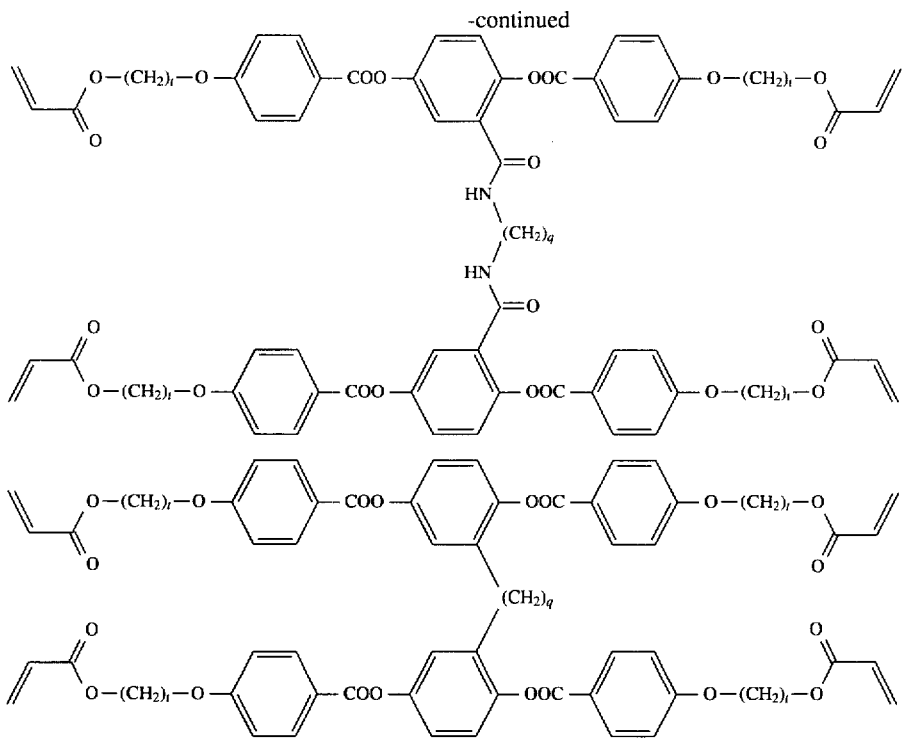
wherein
t is a whole number of 3 to 12;
q is a whole number of 2 to 12; and
X is hydrogen, lower alkyl, fluorine or chlorine.

UNITED STATES PATENT AND TRADEMARK OFFICE
CERTIFICATE OF CORRECTION

PATENT NO. : 5,593,617
DATED : January 14, 1997
INVENTOR(S) : Stephen Kelly and Teodor Lukác It is certified that error appears in the above-indentified patent and that said Letters Patent is hereby corrected as shown below:

In claim 3, column 21, line 50, replace "$(CH_2)3$" with -- $(CH_2)3O$ --.

Signed and Sealed this

Twenty-ninth Day of July, 1997

Attest:

Attesting Officer

BRUCE LEHMAN

Commissioner of Patents and Trademarks